United States Patent [19]
Eoga

[11] 4,409,118
[45] Oct. 11, 1983

[54] TABLET FORMING CLEANSER COMPOSITION AND METHOD OF PREPARATION

[75] Inventor: Anthony B. J. Eoga, Boonton, N.J.

[73] Assignee: Warner-Lambert Company, Morris Plains, N.J.

[21] Appl. No.: 380,157

[22] Filed: May 20, 1982

Related U.S. Application Data

[63] Continuation-in-part of Ser. No. 297,892, Aug. 31, 1981, Pat. No. 4,362,639, which is a continuation-in-part of Ser. No. 251,030, Apr. 3, 1981.

[51] Int. Cl.³ .......................... C11D 7/14; C11D 7/16; C11D 7/18; C11D 7/30
[52] U.S. Cl. ...................................... 252/99; 252/174; 252/174.23; 252/350; 252/DIG. 16
[58] Field of Search ............ 23/313 R; 264/118, 122, 264/127; 252/99, 174, 174.23

[56] References Cited

U.S. PATENT DOCUMENTS

| | | | |
|---|---|---|---|
| 3,227,790 | 1/1966 | Bretschneider | 264/117 |
| 3,337,466 | 8/1967 | Puetzer | 252/99 |
| 3,340,152 | 9/1967 | Hotko | 424/35 |
| 3,458,446 | 7/1969 | Diaz | 252/99 |
| 3,558,497 | 1/1971 | Lawes | 252/99 |
| 3,704,227 | 11/1972 | Hill | 252/95 |
| 3,928,524 | 12/1975 | Leverett | 264/117 |

Primary Examiner—Dennis L. Albrecht
Attorney, Agent, or Firm—Daniel A. Scola, Jr.; Stephen Raines

[57] ABSTRACT

A cleansing composition is disclosed that is particularly suited for compaction into tablet form, and comprises a phosphate salt, an optionally added silicate salt, such as a metasilicate and at least one perborate salt, wherein at least a portion of the perborate salt component is present as a compacted, granulated mixture with from about 0.01% to about 0.70% by weight of the perborate salt, of a polymeric fluorocarbon. Preferably, the perborate salt includes sodium perborate monohydrate and anhydrous sodium perborate, and polytetrafluoroethylene comprises the polymeric fluorocarbon used to prepare the granules.

When present, the silicate salt is preferably utilized within a particle size ranging from about 1 to about 25 microns. The silicate aids disintegration and assists in mechanical cleaning, when the composition is prepared in tablet form for use as a denture cleanser.

The use of the perborate granules reduces the difficulty of compacting the composition to form tablets, without impeding the operation and activity of the tablets as effervescent cleansers.

37 Claims, No Drawings

TABLET FORMING CLEANSER COMPOSITION AND METHOD OF PREPARATION

CROSS-REFERENCE TO RELATED APPLICATIONS

The present application is a continuation-in-part of my copending application Ser. No. 297,892, now U.S. Pat. No. 4,362,639 filed Aug. 31. 1981, which is in turn a continuation-in-part of my copending application Ser. No. 251,030, filed Apr. 3, 1981.

BACKGROUND OF THE INVENTION

1. Field of the Invention

The present invention relates generally to cleansing compositions, and more particularly to cleansing compositions that are prepared in tablet form for use.

2. Description of the Prior Art

Cleanser compositions, and in particular those compositions having utility for hard surface cleaning applications, have utilized oxidizing agents and bleaching agents in concert to remove visible stains, while at the same time providing the capability for the removal of scale or plaque buildup on the surfaces. Thus, a variety of cleansing compositions are known and have been prepared either with abrasive materials for use as scouring cleansers or alone for purpose of mild surface cleaning applications such as passive dispersion in a liquid medium such as water, for soaking applications, such as the cleaning of dentures. All of these compositions have employed a variety of sulfate salts, such as bisulfates, monopersulfates, and sulfates as detergents, oxidizers and the like, and have also utilized alkali metal and alkaline earth metal halides as bleaches. Such compositions have also included perborate, carbonate and phosphate salts in varying amounts, to provide effervescence and activation. Representative cleansing compositions covering these various applications are set forth in U.S. Pat. No. 3,337,466 to Puetzer et al., U.S. Pat. No. 3,458,446 to Diaz, U.S. Pat. No. 3,558,497 to Lawes, U.S. Pat. No. 3,704,227 to Hill, and Applicant's copending applications, Ser. Nos. 251,030 and 297,892, all of which are incorporated herein by reference.

In the instance where the cleansing compositions mentioned above contain one or more perborate salts, and the compositions are prepared into tablets by compression, the compositions have presented certain drawbacks in that they are difficult to compress, and the resulting tablets lack mechanical strength. These problems are owing primarily to physical properties of the perborate salts employed. In particular, anhydrous sodium perborate, which has been utilized in the compositions in my copending applications, is commercially available as a fluffy powder having a low specific weight and density and therefore resistant to compaction and agglomeration. To a lesser extent, this same difficulty is experienced with another perborate salt additive, sodium perborate monohydrate.

Prior attempts to remedy these deficiencies have focused upon the addition of greater amounts of standard tableting aids such as talc, sodium benzoate, and the like. The addition of greater amounts of these ingredients, however, while remedying the difficulties of initial processing and tablet formation, carry with them certain other drawbacks, namely that the formed tablets exhibit retarded action in use, that renders them less commercially desirable. In particular, the increased amounts of tableting aids tend to prolong the disintegration time of the tablet, with the result that the activity of the tablet is delayed and in some instances slightly suppressed, and therefore less attractive to potential consumers.

A process is disclosed in U.S. Pat. No. 4,115,519 to Brichard et al., for the manufacture of sodium perborate monohydrate, that purportedly results in the preparation of granules of the monohydrate possessing the desired particle size, specific weight, abrasion resistance and flowability sought for use in connection with the compaction of dental cleanser tablets. The technique disclosed by the patent, however, is complex and costly, and requires specialized apparatus to conduct a fluidized bed particle formation in contact with hydrogen peroxide. The patentees refer to prior art processes for the formation of the monohydrate salt, and indicate that those processes, as well, are complex and expensive, and frequently yield particles that are unsuitable for the present applications.

U.S. Pat. No. 3,340,152, to Hotko, discloses that polyfluorocarbons may be utilized in the manufacture of tablets, as lubricants, and in amounts by weight of the tableting composition, ranging from about 1% to about 15% by weight, to supplant such known lubricants as magnesium stearate, sodium lauryl sulfate, polyethylene glycols and the like. Hotko suggests that the fluoropolymer may be added directly to the tableting mixture, in its capacity and amount as a lubricant, and purportedly has a favorable effect on the tablet-forming process. There is no disclosure in Hotko that the fluoropolymers would serve as agglomeration or compaction aids, to facilitate the preparation of granulated materials of increased and improved specific weight.

A need therefore exists for the preparation and employment of a granulated perborate salt that is easily and efficiently compressed in combination with the remaining ingredients of cleansing compositions, to enable the compositions to be formed into cleanser tablets that exhibit mechanical stability without reduced activity.

SUMMARY OF THE INVENTION

In accordance with the present invention, a cleansing composition is prepared that is particularly suited for compression into tablet form. The cleansing composition comprises a phosphate salt in an amount from about 20% to about 45% by weight, an optional silicate salt in particulate form, in an amount of up to about 20% by weight and at least one perborate salt in an amount of at least 50% by weight, wherein at least a portion of the perborate salt is present as a compacted, granulated mixture with from about 0.01% to about 0.70% by weight of the salt, of a polymeric fluorocarbon.

The mixture of the perborate salt and the polymeric fluorocarbon is prepared by compaction, such as by slugging or roller compaction, followed by comminution under agitation to form granules that may, for example, have a particle size capable of passing through a 30 mesh screen.

Preferably, the phosphate salt comprises an alkali metal phosphate, such as trisodium phosphate, present in an amount of from about 25% to about 40% by weight. The silicate salt comprises an alkali metal metasilicate such as sodium metasilicate, and may be present in an amount from about 10% to about 20% by weight. Further, the silicate salt should have a particle size on the order of 1 micron to about 25 microns, as this particle size range enables the quantities of the silicate salt utilized herein to be included, without adverse effect upon the disintegration time of a tablet prepared from the present composition.

The perborate salts utilized in the present composition may comprise alkali metal perborates selected from the group consisting of alkali metal perborate monohydrates and anhydrous alkali metal perborates. In particular, the sodium salts are contemplated, and the present compositions may contain from about 50% to about 70% by weight of the perborate salts. Preferably, the compositions contained from about 50% to about 65% by weight of the perborate salts, including at least 20% by weight of the anhydrous alkali metal perborate.

The polymeric fluorocarbon is preferably present in an amount of from about 0.33% to about 0.66% by weight of the perborate salt, and may include at least one fluoroolefin. Preferably, the polymeric fluorocarbon comprises polytetrafluoroethylene, and the perborate salt prepared in compacted, granular form, comprises the anhydrous alkali metal perborate.

The present cleansing compositions may also include other ingredients such as colorants, detergents, pH adjustment additives, perfumes and the like, and are particularly useful when prepared in tablet form for use, for example, as denture cleansers.

The present invention also relates to a method for preparing the effervescing cleansing composition, comprising preparing a perborate salt in a compacted, granular mixture with a polymeric fluorocarbon, in which the polymeric fluorocarbon is present in an amount by weight of the perborate salt, ranging from about 0.01% to about 0.70%, adding to the perborate salt a quantity of a phosphate salt and a silicate salt, whereby the phosphate salt is present in an amount by weight of the total composition of from about 20% to about 45%, the silicate salt is present in an amount of up to about 20% by weight, and the perborate salt is present in an amount of at least 50% by weight, all to form a second mixture, and compacting the second mixture to form a plurality of tablets therefrom. Preferably, the silicate salt comprises an alkali metal metasilicate having a particle size ranging from about 1 micron to about 25 microns, the perborate salt comprises a mixture of sodium perborate monohydrate and anhydrous sodium perborate, and the phosphate salt comprises trisodium phosphate.

Accordingly, it is a principal object of the present invention to provide an effervescing cleanser composition capable of serving as a denture cleanser in tablet form.

it is a further object of the present invention to provide a cleanser composition as aforesaid, that is easily molded into tablets that retain their mechanical stability and strength.

It is a still further object of the present invention to provide a cleanser composition as aforesaid, that is promptly activated upon placement in water.

It is a still further object of the present invention to provide a method for the preparation of the present cleansing compositions, which is simple and inexpensive.

Other objects and advantages will become apparent to those skilled in the art from a consideration of the ensuing detailed description.

DETAILED DESCRIPTION

The cleansing compositions of the present invention comprise a phosphate salt in an amount of from about 20% to about 45% by weight. Preferably, the phosphate salt may be present in an amount ranging from about 25% to about 40% by weight, and comprises alkali metal phosphates and alkaline earth metal phosphates, with alkali metal phosphates preferred. More particularly, the alkali metal phosphate may comprise trisodium phosphate.

The phosphate component serves as a cleaner, and in the instance where the present compositions are utilized as denture cleansers, attacks and disintegrates the dental plaque that forms on the surface of the dentures. This cleaning role is in addition to the function of the phosphates as builders.

The silicate salt may be added to the present compositions to serve as a mechanical cleaner, as it is believed that the silicate exerts some mild abrasive action upon the surface of the dentures, that causes the breakup of the dental plaque and other scale that may have formed thereon during use. The silicate salt preferably comprises an alkali metal metasilicate, such as sodium metasilicate. Naturally, the invention includes other metasilicates within its scope, and should not be limited to the specific metasilicate disclosed herein.

The silicate salt may be added in an amount of up to about 20% by weight of the composition, and preferably in an amount of from about 10% to about 20% by weight. When utilized, the silicate salt is provided in particulate form, with particle sizes that should range between 1 micron and 25 microns in size. The adherence to this size limitation is important, as the metasilicates lying outside this particle size range, tend to adversely effect the activity of the present composition, when it is prepared in tablet form.

More particularly, earlier efforts to utilize metasilicate salts with particle sizes lying outside the aforementioned range, resulted in the preparation of tablets that exhibited disintegration delays so excessive as to render the tablets commercially unusable. In some instances, the metasilicate appeared to completely block disintegration, and had to be deleted.

It is therefore one of the features of the present invention, that the use of a metasilicate component having the particle size range disclosed herein, poses no obstacle to the disintegration of tablets prepared from such a composition.

The present compositions may also contain at least one perborate salt in an amount of at least 50% by weight. The perborate salt functions in a variety of capacities within the present compositions, as it provides cleaning action, as well as promoting the activity of the compositions by initiating effervescence as well as inhibiting tarnish and corrosion of susceptible substrates immersed in solutions of the present composition.

The perborate salts may be selected from alkali metal perborates and alkaline earth metal perborates, and more particularly may be selected from alkali metal perborate monohydrate and anhydrous alkali metal perborates. Thus, the sodium and potassium salts of the perborate monohydrate and anhydrous perborates may be utilized, and preferably, the perborate salts may comprise sodium perborate monohydrate and anhydrous sodium perborate.

The perborate salts are preferably present in an amount ranging from about 50% to about 70% by weight of the composition, and more preferably from about 50% to about 65% by weight. The perborate salts may comprise a mixture of the anhydrous perborate and the perborate monohydrate, in which instance the anhydrous perborate is present in an amount of at least 20% by weight, and preferably in an amount from about 20% to about 25% by weight.

A further feature of the present compositions, comprises the preparation of at least a portion of the perborate salt in a compacted, granulated mixture with from about 0.01% to about 0.70% by weight of the salt, of a polymeric fluorocarbon. The preparation of this compacted granular mixture and its employment in the present composition is particularly noteworthy, as it facilitates the compaction of the perborate salt without adversely effecting the properties and activity of tablets prepared from the composition. Perborate salts, and in particular, anhydrous sodium perborate, are extremely light, fluffy materials having a low specific weight, that have been difficult to compact when attempts to incorporate this material in denture cleanser tablets, for example, have been made. Thus, the perborate component has tended to stick to the tablet dies, and tablets prepared with the perborate have been extremely frangible and therefore commercially undesirable. Prior art attempts to remedy this deficiency by the addition of greater quantities of conventional tableting aids, have resulted in the preparation of tablets that, while dimensionally stable and mechanically strong, exhibit greatly diminished activity when placed in solution. Thus, disintegration times are undesirably prolonged, and in some instances disintegration does not take place.

As discussed earlier herein, U.S. Pat. No. 3,340,152 to Hotko, describes the use of a polymeric fluorocarbon as a lubricant in tablet formation. Efforts to utilize the polymeric fluorocarbons disclosed by hotko within the ranges set forth in the patent, proved fruitless, as the resulting tablets, while dimensionally stable, exhibited little or no activity in solution. Likewise, efforts to place even reduced amounts of the polymeric fluorocarbons in direct combination with the ingredients of cleansers such as those presently disclosed, resulted in the preparation of tablets having similar drawbacks. Accordingly, the preparation of the perborate salts in the manner disclosed in the present invention is important to the preparation of compositions in tablet form, that possess the property of dimensional stability and ease of preparation, in combination with retention of desirable solution activity. Thus, tablets prepared by the present invention disintegrate as quickly, and in some instances more quickly than acceptable denture tablets prepared in accordance with the prior art.

The mixture of the perborate salts with the polymeric fluorocarbon may include the fluorocarbon in an amount preferably ranging from about 0.33% to about 0.66% by weight of the perborate salt. The polymeric fluorocarbon may be selected from a well known group of polymeric and copolymeric substances made up of carbon and fluorine, which, in addition, may contain hydrogen and/or chlorine. The fluorocarbon may include at least one fluoroolefin; for example, polytetrafluoroethylene, copolymers of tetrafluoroethylene and hexafluoropropylene, and copolymers of vinylidene fluoride and hexafluoropropylene would be included. The preferred polymeric fluorocarbon comprises polytetrafluoroethylene.

The fluorocarbon polymers may be utilized in the form of powders having particle sizes acceptable for combination with the perborate salts, and preferably ranging up to about 150 microns in size. The exact particle size may vary, and an average particle size of from about 25 to about 75 microns may be used. The exact particle size of the polymeric fluorocarbon is not critical to the practice of the present invention.

The preparation of the perborate salt-polymeric fluorocarbon mixture into compact granules may be conducted by compaction on a continuous or batch basis, by means, for example, of a roller compactor or a tablet slugging machine, to form a plurality of preforms such as flakes or slugs. Preforms would thereafter be subjected to comminution under agitation to form the desired particles, and may possess particle sizes ranging on the order of 30 mesh or greater. The exact details of the preparation of the compacted perborate salt particles is disclosed in my copending application Ser. No. 380,164, the disclosure of which is incorporated herein by reference.

In addition to the ingredients set forth above, the present compositions may contain a variety of additional ingredients selected on the basis of desired end use. Thus, for example, the compositions may include detergent compounds, such as organic and inorganic detergents, including non-ionic detergents such as the various polyoxyethylene ethers of aromatic and aliphatic alcohols, as well as the polyoxyethylene ethers of hydrophobic propylene oxide polymers. These compounds assist in maintaining a foaming action, in the instance where the cleansing compositions are placed in aqueous solution.

Also, the compositions may contain other adjuvant materials, that may be inorganic or organic in structure. Thus, inorganic water-soluble alkaline builders such as alkali and alkaline earth metal carbonates, hydroxides, and mixtures may be added. Particularly, sodium carbonate may be present in an amount of up to about 2% by weight, as it functions not only as a builder, but enhances effervescence and assists in stabilizing the pH of the solutions obtained from the composition.

The present compositions may also contain sequestrants for the purpose of maintaining solution clarity, in the instance where the compositions are placed in solution. The sequestrants may also assist in the inhibition of corrosion and tarnish of particles soaked in solutions containing the present compositions. Useful sequestrants include ethylene diamine tetracedic acid (EDTA) and its corresponding alkali salts, as well as other polyfunctional organic acids, such as citric acid, maleic acid and their corresponding salts. The sequestrants may be present in amounts of up to about 3% by weight.

In the instance where the composition is to be prepared for use as a denture cleanser, other additives such as flavorings, colorants, perfumes and the like may be added in various amounts, as mentioned earlier. For example, the flavorings may include varieties of mint, oil of clove, artificial vanilla flavoring, and others. These materials may be included and blended in various combinations within the scope of the present invention. The choice of the required amounts is likewise within the skill of the art.

In the instance where the present cleansing compositions are formulated for use as denture cleansers, the colorants useful herein are those known as F.D.&C. and D.&C. dyes and lakes. These materials are certified by the Federal Food and Drug Administration as acceptable for use in food, drug and cosmetic applications, and drug and cosmetic colorings. The materials acceptable for the foregoing spectrum of use are preferably water-soluble, and include indigoid dye, known as F.D.&C. Blue No. 2, which is the disodium salt of 5,5'-indigotindisulfonic acid. Similarly, the dye known as F.D.&C. Green No. 1, comprises a triphenylmethane dye and is the monosodium salt of 4-[4-(N-ethyl-p-sulfobenzylamino)diphenylmethylene]-[1-(N-ethyl-N-p-sulfoniumbenzyl)-$\Delta^{2,5}$-cyclohexadienimine]. A full recitation of all F.D.&C. and D.&C. and their corresponding chemical structures may be found in the Kirk-Othmer Encyclopedia of Chemical Technology, at Volume 5, pages 857–884, which text is accordingly incorporated herein by reference. Dyes and colorants will fade at different rates and may be chosen to provide specific end points.

The foregoing colorants may be blended with each other in a variety of combinations. It is particularly desirable that the colorants be chosen so that the composition when initially dissolved will present a deep hue. This is important in the instance where the composition serves as a denture cleanser, as the fading phenomenon embodied in denture cleansers can be more easily observed by the end user.

The present invention includes a method for the preparation of the compositions, which comprises preparing at least a portion of the perborate salt component as a first mixture, including the polymeric fluorocarbon, and compacting the first mixture to form a plurality of particles thereof. The remainder of the ingredients, including the silicate salt prepared with a particle size within the aforementioned ranges, are then combined to form a second mixture which may be prepared in tablet form, in the instance, for example, where the present compositions are to be utilized as denture cleansers. It is preferable to prepare the present compositions in tablet form in such instance, as it is easier to achieve the uniformity of quantity and distribution of the ingredients of the compositions that is necessary to assure the corresponding uniformity of performance of the cleanser. Thus, cleanser tablets have been found to exhibit uniformity of color reaction, disintegration and fade time, in cleaning ability on a tablet-to-tablet basis.

In accordance with the present invention, the compositions may be prepared in tablet form without the need for increased addition of ingredients such as excipients, tableting agents and the like. While such ingredients may be added, the amounts of these ingredients may be reduced, due to the favorable effect exerted by the polymeric fluorocarbon present in the compacted granules of the perborate salt. Naturally, minor additional quantities of ingredients such as the polymeric fluorocarbon, may be made for their stated purpose, such as for lubrication and the like, however such additions and their respective amounts are not critical and do not form a part of the present invention.

A fuller understanding of the present invention will be gained from a review of the following illustrative examples. Unless specified otherwise, all amounts expressed as percent, are intended to be a percent by weight.

EXAMPLES I–IV

A series of cleanser compositions were prepared having the ingredients set forth in Table I, below.

TABLE I

| INGREDIENTS | AMOUNT (WEIGHT %) | | | |
|---|---|---|---|---|
| | I | II | III | IV |
| Sodium Perborate Monohydrate | 33.7 | 39.3 | 33.7 | 33.7 |
| Trisodium Phosphate | 24.6 | 32.3 | 41.3 | 24.7 |
| Sodium Metasilicate | 16.7 | — | — | 16.7 |

TABLE I-continued

| INGREDIENTS | AMOUNT (WEIGHT %) | | | |
|---|---|---|---|---|
| | I | II | III | IV |
| Anhydrous Sodium Perborate | 20.1* | 23.7** | 20.2*** | 20.0* |
| Polytetrafluoroethylene | .26 | — | .29 | .23 |
| Ethylene Diamine Tetracidic Acid Tetrasodium Salt | 2.6 | 1.3 | 2.6 | 2.7 |
| Colorant | .23 | .17 | .23 | .23 |
| Flavor and Fragrance | .53 | .70 | .53 | .53 |
| Sodium Benzoate | 1.0 | .70 | 1.1 | 1.1 |
| Detergent | .17 | .14 | .17 | .17 |
| Magnesium Stearate | .02 | .03 | — | .02 |
| Sodium Carbonate | — | 1.7 | — | — |

*Includes .33% by weight of perborate, of polytetrafluoroethylene, prepared as granulated mixture.
**Includes .60% polytetrafluoroethylene, in granulated mixture.
***Includes .66% polytetrafluoroethylene, in granulated mixture.

The compositions were prepared as follows. Initially, a quantity of anhydrous sodium perborate in the form of a fluffy powder, was combined in a container with a quantity of polytetrafluoroethylene powder identified as Grade F5A by the E.I. duPont DeNemours & Co., Inc. The polytetrafluoroethylene was added in the amounts based upon the weight of the perborate, as indicated with respect to each of the examples, above. Blending was performed for about 3 minutes, after which the mixture was compressed by passing through a tablet slugging machine having 27/32" dies. The slugs were then passed through an oscillating granulator having a 16 mesh screen, to form the granules of the anhydrous perborate/tetrafluoroethylene mixture.

The remaining ingredients of the composition were added to the perborate, the phosphate added first, to form the second mixture. In the instance where metasilicate was added, a powder having a particle size ranging from 10 to 25 microns was used. The resulting second mixture was stirred and thereby blended for a period of about 3 minutes, after which the mixture was formed into tablets by compression in a tablet slugging machine having a tablet die of 27/32". The tablets were formed to a hardness ranging from about 20 to about 30 S.C.U., and were thereafter cured in a hot air oven for 45 minutes at 95° C.

After the preparation of the tablets was complete, representative tablets from each of the four formulations were tested for activity and efficacy, by placement in individual containers having approximately 120 milliliters of water at 45° C.

Each of the compositions tested, exhibited a disintegration time of approximately 90 seconds, a pH ranging up to about 11.2, and a fade time of approximately 5 minutes. It was determined that each of the compositions could thus be prepared into tablets for use as denture cleansers, with satisfactory activity and efficacy.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. An effervescent cleansing composition in tablet form comprising:
   A. a phosphate salt in an amount of from about 20% to about 45% by weight;

B. a silicate salt in an amount of up to about 20% by weight; and

C. at least one perborate salt in an amount of at least 50% by weight:

wherein at least a portion of said perborate salt is present in a compacted, granulated mixture in an amount effective to facilitate compaction without substantially sticking to tablet forming equipment and with suitable dimensional stability without prolonged disintegration time when placed in solution, said granulated mixture containing from about 0.01% to about 0.70% by weight of said granulated mixture of a polymeric fluorocarbon.

2. The composition of claim 1 wherein said phosphate salt comprises an alkali metal phosphate.

3. The composition of claim 2 wherein said phosphate salt comprises trisodium phosphate.

4. The composition of claims 1, 2 or 3 wherein said phosphate salt is present in an amount of from about 25% to about 40% by weight.

5. The composition of claim 1 wherein said silicate salt comprises an alkali metal metasilicate.

6. The composition of claim 5 wherein said alkali metal metasilicate comprises sodium metasilicate.

7. The composition of claims 5 or 6 wherein said silicate salt is present in an amount of from about 10% to about 20% by weight.

8. The composition of claims 5 or 6 wherein said silicate salt has a particle size of from about 1 micron to about 25 microns.

9. The composition of claim 1 wherein said perborate salt is selected from the group consisting of alkali metal and alkaline earth metal perborates.

10. The composition of claim 9 wherein said perborate salt comprises an alkali metal perborate.

11. The composition of claim 10 wherein said alkali metal perborate is selected from the group consisting of alkali metal perborate monohydrates and anhydrous alkali metal perborates.

12. The composition of claim 11 wherein said alkali metal perborates comprise sodium perborate.

13. The composition of claim 12 wherein said perborate salt is present in an amount of from about 50% to about 70% by weight.

14. The composition of claim 13 wherein said perborate is present in an amount of from about 50% to about 65% by weight.

15. The composition of claims 1, 13 or 14 wherein said perborate salt includes at least 20% by weight of an anhydrous alkali metal perborate.

16. The composition of claim 15 wherein said anhydrous perborate is present in an amount of from about 20% to about 25% by weight.

17. The composition of claim 15 wherein said anhydrous perborate comprises anhydrous sodium perborate.

18. The composition of claim 16 wherein said anhydrous perborate comprises anhydrous sodium perborate.

19. The composition of claim 1 wherein said polymeric fluorocarbon includes at least one fluoroolefin.

20. The composition of claim 19 wherein said polymeric fluorocarbon comprises polytetrafluoroethylene.

21. The composition of claims 1, 19 or 20 wherein said polymeric fluorocarbon is present in an amount from about 0.33% to about 0.66% by weight.

22. The composition of claim 13 wherein said polymeric fluorocarbon includes at least one fluoroolefin.

23. The composition of claim 15 wherein said polymeric fluorocarbon includes at least one fluoroolefin.

24. The composition of claim 22 wherein said polymeric fluorocarbon comprise polytetrafluoroethylene.

25. The composition of claim 23 wherein said polymeric fluorocarbon comprises polytetrafluoroethylene.

26. The composition of claim 13 wherein said polymeric fluorocarbon is present in an amount from about 0.33% to about 0.66% by weight.

27. The composition of claim 15 wherein said polymeric fluorocarbon is present in an amount from about 0.33% to about 0.66% by weight.

28. The composition of claim 22 wherein said polymeric fluorocarbon is present in an amount from about 0.33% to about 0.66% by weight.

29. The composition of claim 23 wherein said polymeric fluorocarbon is present in an amount from about 0.33% to about 0.66% by weight.

30. The composition of claim 1 further including at least one material selected from the following: builders, detergents, lubricants, sequestrants, perfumes, flavorings, excipients, disintegrants, and mixtures thereof.

31. The composition of claim 30 wherein said sequestrant comprises ethylene diamine tetracidic acid and its alkali metal salts, and said builders include sodium carbonate.

32. The tablet of claim 1 useful as a denture cleanser comprising the composition of claims 1, 5 or 12.

33. The tablet of claim 1 useful as a denture cleanser comprising the composition of claim 4.

34. The tablet of claim 1 useful as a denture cleanser comprising the composition of claim 7.

35. The tablet of claim 1 useful as a denture cleanser comprising the composition of claim 13.

36. The tablet of claim 1 useful as a denture cleanser comprising the composition of claim 15.

37. The tablet of claim 1 useful as a denture cleanser comprising the composition of claim 19.

* * * * *